US012570886B2

(12) United States Patent
Tortelli et al.

(10) Patent No.: US 12,570,886 B2
(45) Date of Patent: Mar. 10, 2026

(54) HEAT EXCHANGE METHOD USING FLUORINATED COMPOUNDS HAVING A LOW GWP

(71) Applicant: SYENSQO SPECIALTY POLYMERS ITALY S.p.A, Bollate (IT)

(72) Inventors: Vito Tortelli, Milan (IT); Emanuela Antenucci, Saronno (IT); Cristiano Monzani, Trezzo sull'Adda (IT); Letanzio Bragante, Due Carrare (IT); Valeriy Kapelyushko, Alessandria (IT)

(73) Assignee: SYENSQO SPECIALTY POLYMERS ITALY S.p.A., Bollate (IT)

( * ) Notice: Subject to any disclaimer, the term of this patent is extended or adjusted under 35 U.S.C. 154(b) by 575 days.

(21) Appl. No.: 17/619,090

(22) PCT Filed: Jul. 7, 2020

(86) PCT No.: PCT/EP2020/069155

§ 371 (c)(1),
(2) Date: Dec. 14, 2021

(87) PCT Pub. No.: WO2021/008949

PCT Pub. Date: Jan. 21, 2021

(65) Prior Publication Data

US 2022/0259477 A1 Aug. 18, 2022

(30) Foreign Application Priority Data

Jul. 18, 2019 (EP) .................................... 19187012

(51) Int. Cl.

| | |
|---|---|
| ***C09K 5/10*** | (2006.01) |
| ***C07C 43/12*** | (2006.01) |
| ***H01L 21/67*** | (2006.01) |
| ***H01L 23/00*** | (2006.01) |
| ***H01M 10/613*** | (2014.01) |
| ***H01M 10/625*** | (2014.01) |
| ***H01M 10/6567*** | (2014.01) |
| ***H05K 7/20*** | (2006.01) |
| ***H10P 72/00*** | (2026.01) |
| *H10W 72/00* | (2026.01) |

(52) U.S. Cl.

CPC .............. *C09K 5/10* (2013.01); *C07C 43/126* (2013.01); *H01M 10/613* (2015.04); *H01M 10/625* (2015.04); *H01M 10/6567* (2015.04); *H05K 7/20236* (2013.01); *H05K 7/20763* (2013.01); *H10P 72/0434* (2026.01); *H01M 2220/20* (2013.01); *H10W 72/07334* (2026.01); *H10W 72/07336* (2026.01); *H10W 72/07341* (2026.01)

(58) Field of Classification Search

CPC .... C09K 5/10; H01M 10/613; H01M 10/625; H01M 10/6567; H01M 2220/20; C07C 43/126; H01L 21/67109; H01L 24/83; H01L 2224/83075; H01L 2224/8321; H01L 2224/83815; H05K 7/20236; H05K 7/20763

USPC .......................................................... 429/120

See application file for complete search history.

(56) References Cited

U.S. PATENT DOCUMENTS

| | | | | |
|---|---|---|---|---|
| 5,713,211 | A | 2/1998 | Sherwood | |
| 6,019,909 | A | 2/2000 | Ide et al. | |
| 6,136,331 | A | 10/2000 | Morita et al. | |
| 2005/0126756 | A1 | 6/2005 | Costello et al. | |
| 2005/0253107 | A1* | 11/2005 | Flynn | C09K 5/041 252/67 |
| 2006/0131737 | A1* | 6/2006 | Im | H01L 23/473 257/E23.098 |

(Continued)

FOREIGN PATENT DOCUMENTS

| | | | |
|---|---|---|---|
| EP | 0344935 | A2 | 12/1989 |
| GB | 1450467 | A | 9/1976 |

(Continued)

OTHER PUBLICATIONS

Hodnebrog Ø. et al., "Global warming potentials and radiative efficiencies of halocarbons and related compounds: A comprehensive review", Review of Geophysics, 2013, vol. 51, p. 300-378.

(Continued)

*Primary Examiner* — Allison Bourke
*Assistant Examiner* — Robert Gene West
(74) *Attorney, Agent, or Firm* — Osha Bergman Watanabe & Burton LLP

(57) ABSTRACT

The present invention relates to a method for exchanging heat with an object said method comprising using a heat transfer fluid wherein said heat transfer fluid comprises one or more chemical compounds having the general formula: (I) wherein:

$R_1$, $R_2$, $R_3$, $R_4$ can be the same or different, linear or branched, partially fluorinated alkyl groups having a C1-C6 carbon chain.

(I)

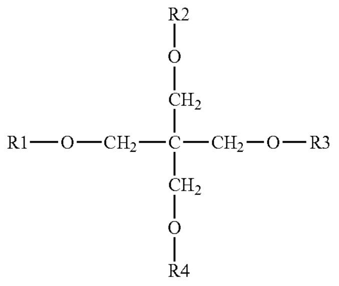

10 Claims, No Drawings

(56) References Cited

U.S. PATENT DOCUMENTS

| | | | | |
|---|---|---|---|---|
| 2007/0187639 | A1 | 8/2007 | Leck et al. | |
| 2008/0160419 | A1 | 7/2008 | Segawa et al. | |
| 2014/0174084 | A1* | 6/2014 | Kontomaris | C09K 5/048<br>60/671 |
| 2015/0236386 | A1* | 8/2015 | Yang | H01M 10/658<br>165/104.21 |
| 2016/0044833 | A1* | 2/2016 | Krishnan | H05K 7/203<br>165/80.4 |

FOREIGN PATENT DOCUMENTS

| | | | | | |
|---|---|---|---|---|---|
| JP | 8040964 | A | | 2/1996 | |
| JP | 8151586 | A | | 6/1996 | |
| JP | 8151587 | A | | 6/1996 | |
| JP | 9318182 | A | | 12/1997 | |
| JP | 10168474 | A | * | 6/1998 | |
| WO | 9534613 | A1 | | 12/1995 | |
| WO | 2007099055 | A2 | | 9/2007 | |
| WO | 2010034698 | A1 | | 4/2010 | |
| WO | WO-2016064585 | A1 | * | 4/2016 | C07C 69/63 |

OTHER PUBLICATIONS

England, D. C. et al., “Nucleophilic reactions of fluoroolefins”, Journal of the American Chemical Society, 1960, 82, 5116-22.

Sievert, A. C. et al., “Synthesis of perfluorinated ethers by an improved solution phase direct fluorination process”, Journal of Fluorine Chemistry, 1991, 53(3), 397-417, Elsevier Sequoia, Lausanne.

* cited by examiner

HEAT EXCHANGE METHOD USING FLUORINATED COMPOUNDS HAVING A LOW GWP

TECHNICAL FIELD

This application is a U.S. national stage entry under 35 U.S.C. § 371 of International Application No. PCT/EP2020/069155 filed Jul. 7, 2020, which claims priority to European Application No. 19187012.0, filed on Jul. 18, 2019. The entire contents of these applications are explicitly incorporated herein by this reference.

The present invention relates to a method for exchanging heat with an object using compositions comprising selected fluorinated compounds having low GWP as heat transfer fluids.

BACKGROUND ART

Heat transfer fluids are known in the art for applications in heating and cooling systems; typically, heat transfer fluids include water, aqueous brines, alcohols, glycols, ammonia, hydrocarbons, ethers and various halogen derivatives of these materials, such as chlorofluorocarbons (CFCs), hydrochlorofluorocarbons (HFCs), (per)fluorinated polyethers (PFPEs) and the like.

Heat transfer fluids are used to transfer heat from one body to another, typically from a heat source to a heat sink so as to effect cooling of the heat source, heating of the heat sink or to remove unwanted heat generated by the heat source. The heat transfer fluid provides a thermal path between the heat source and the heat sink; it may be circulated through a loop system or other flow system to improve heat flow or it can be in direct contact with heat source and heat sink. Simpler systems use simply an airflow as heat transfer fluid, more complex system use specifically engineered gases or liquids which are heated or refrigerated in a portion of the system and then are delivered in thermal contact with the destination.

Computing equipment such as computers, servers and the like generate substantial amounts of heat. Massive developments concentrating a large number of computers operating in shared locations such as server farms are getting more and more common. The industry of server farms, bitcoin mining farms and other supercomputing applications is growing extremely fast. A key factor in determining the building strategy of such installations is a control system which allows exchanging heat with such computing equipment. This system, often called "thermal management system", is typically used for cooling the computing equipment during its operation, but it can also be used for heating e.g. when starting up a system in a cold environment. Air is still the most commonly used fluid which however has the drawback to require large air gaps between electronic boards, which causes the installation to have very large footprints. Air cooling also requires massive air conditioning engines and their energy consumption is extremely high and represents a significant portion of the running costs for such installations.

Recently, solutions for thermal management of servers based on the use of heat transfer fluids, especially liquid heat transfer fluids are getting a lot interest because they are both energy efficient (use less energy than traditional air conditioning systems) and allow to pack more servers, processors and circuit boards in a smaller space.

Other important specialized applications for heat transfer fluids can be found e.g. in the semiconductor industry (TCUs, thermostatic baths, vapor phase soldering) and in the batteries industry especially in the vehicle battery industry for their thermal management systems.

A variety of heat transfer fluids exist which are used industrially in various application, however the choice of an appropriate fluid can be critical in some applications. Several of the heat transfer fluids commonly used in the past are no longer viable because of their toxicity (ammonia, ethylene glycol), others have been phased out due to their environmental profile because they are not biodegradable and/or because they are considered to be detrimental to the earth ozone layer and/or to act as greenhouse gases if dispersed in the environment.

Fluorinated liquids are very effective heat transfer fluids. Commercial products exist such as Solvay's Galden and 3M's Fluorinert: these are fluids which are dielectric, have a high heat capacity, a low viscosity and are non-toxic and chemically inert so they can get in direct contact with electronic boards and also do not chemically interact with most materials. A drawback associated with these fluorinated fluids used so far is their high GWP value.

GWP (Global Warming Potential) is an attribute which can be determined for a given chemical compound which indicates how much heat a given greenhouse gas can entrap in the atmosphere (considering "1" as the reference value for $CO_2$) and is calculated over a specific interval of time, typically 100 years ($GWP_{100}$).

The determination of $GWP_{100}$ is performed by combining experimental data concerning the atmospheric lifetime of the chemical compound and its radiative efficiency with specific computational tool which are standard in the art and are described e.g. in the extensive review published by Hodnebrog et. Al. in Review of Geophisics, 51/2013, p 300-378. Highly stable halogenated molecules such as $CF_4$ and chloro/fluoro alkanes have a very high $GWP_{100}$ (7350 for $CF_4$, 4500 for CFC-11).

Over the years heat transfer fluids having elevated values of GWP (such as the chloro/fluoro alkanes used in air conditioning systems) have been phased out by the industry and replaced with compounds having a lower $GWP_{100}$ value and there is still a continuous interest in heat transfer fluids having $GWP_{100}$ values which are as low as possible.

Hydrofluoroethers, in particular segregated hydrofluoroethers, tend to have relatively low $GWP_{100}$ values while the rest of their properties can be compared to those of the CFCs used in the past, for this reason some hydrofluoroethers have been used industrially and gained popularity as heat transfer fluids and are marketed e.g. by 3M under the trade name "Novec®".

Hydrofluoroethers are broadly described as heat transfer media due to their wide temperature range where they are liquid, and due to their low viscosity in a broad range of temperatures which makes them useful for applications as low temperature secondary refrigerants for use in secondary loop refrigeration systems where viscosity should not be too high at operating temperatures.

Fluorinated ethers are described for example by 3M in U.S. Pat. No. 5,713,211, by Dupont in US 2007/0187639 and by Solvay Solexis in WO 2007/099055 and WO2010034698.

However, while much lower than CFCs, the $GWP_{100}$ of segregated hydrofluoroethers is still in a range from 70 to 500 as shown in U.S. Pat. No. 5,713,211 (table 5):

| | $GWP_{100}$ |
|---|---|
| $C_4F_9$—O—$CH_3$ | 330 |
| $C_4F_9$—O—$O_2H_5$ | 70 |
| c-$C_6F_{11}$—O—$CH_3$ | 170 |

Other hydrofluoro-olefins have been commercialized as heat transfer fluids e.g. by Chemours (Opteon™) and Honeywell (Solstice™). These compounds have a very low GWP, around 1, but, differently from the formerly cited compounds, are much more flammable and therefore this limits their field of use.

Therefore there is still a need to develop methods for effective heat transfer using heat transfer fluids which have good thermal and dielectric properties, are liquid in a broad range of temperatures, are non flammable, and have very low $GWP_{100}$ (60 and below).

SUMMARY OF INVENTION

In one aspect the present invention relates to a method for exchanging heat with an object said method comprising using a heat transfer fluid wherein said heat transfer fluid comprises one or more chemical compounds having the general formula:

(I)

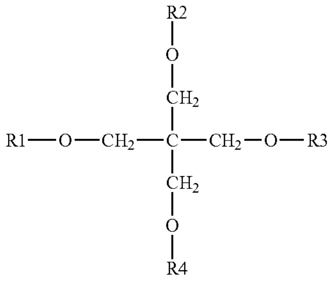

wherein:

$R_1$, $R_2$, $R_3$, $R_4$ can be the same or different, linear or branched, partially fluorinated alkyl groups having a C1-C6 carbon chain.

DESCRIPTION OF EMBODIMENTS

For "electronic computing equipment" it is intended any individual or arrays of individual computer boards comprising microprocessors CPUs, GPUs, SSD and DDR Memory, and performing computational work, thus including both large server farms, internet servers, bitcoin mining factories, but also smaller individual computers, internet servers, computer gaming equipment. Both large and small installation may benefit from the heat transfer method of the present invention.

The term "semiconductor device" in the present invention include any electronic device which exploits the properties of semiconductor materials. Semiconductor devices are manufactured both as single devices and as integrated circuits which consist of a number (which can go from two to billions) of devices manufactured and interconnected on a single semiconductor substrate or "wafer". The term "semiconductor devices" includes both the basic building blocks, such as diodes and transistors, to the complex architectures built from these basic blocks which extend to analog, digital and mixed signal circuits, such as processors, memory chips, integrated circuits, circuit boards, photo and solar cells, sensors and the like. The term "semiconductor devices" also includes any intermediate or unfinished product of the semiconductor industry derived from a semiconductor material wafer.

The present invention relates to a method for exchanging heat with an object said method comprising using a heat transfer fluid wherein said heat transfer fluid comprises one or more chemical compounds having the general formula:

(I)

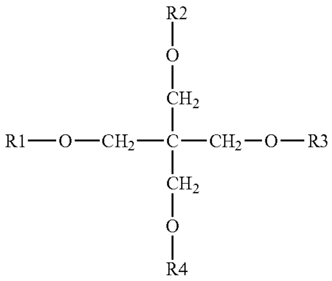

wherein:

- $R_1$, $R_2$, $R_3$, $R_4$ can be the same or different, linear or branched, partially fluorinated alkyl groups having a C1-C6 carbon chain which may contain in chain heteroatoms selected from O and S, if a in chain heteroatom is present this is preferably 0;
- preferably if an oxygen atom is present in any $R_1$, $R_2$, $R_3$, $R_4$ that substituent preferably has a C3-C6 carbon chain
- preferably if no oxygen atoms are present in any of $R_1$, $R_2$, $R_3$, $R_4$ that substituent $R_x$ preferably has a C2-C4 carbon chain
- preferably in each of $R_1$, $R_2$, $R_3$ and $R_4$ the C atom in position 2 is bonded to a H atom, For "partially fluorinated alkyl group" it is intended an alkyl group having at least one C—F bond and at least one C—H bond. Alkyl groups including in chain heteroatoms selected from S and O, such as alkyl groups comprising C—O—C or C—S—C moieties are included in the definition.

Preferably $R_1$, $R_2$, $R_3$ and $R_4$ do not contain in chain heteroatoms, more preferably $R_1$, $R_2$, $R_3$ and $R_4$ are selected from —CF2-CHF2 and —CF2-CHF—CF3.

The most preferred compounds among those encompassed by the general formula (I) are the derivative resulting from the addition of TFE (tetrafluoroethylene) and or HFP (hexafluoropropylene) to pentaeritrytol, respectively $C(CH_2—O—CF_2—CHF_2)_4$ and $C(CH_2—O—CF_2—CHF—CF_3)_4$.

In all embodiments it is preferred that the heat exchange fluid is essentially free of conventional refrigerating gases such as CFCs, HFCs and HCFCs. CFCs are known to have a high $GWP_{100}$ and even in minor amount contribute to the $GWP_{100}$ of the heat exchange fluid more than its main components according to formula (I). HFCs and HCFCs have been developed to offer an improved $GWP_{100}$ profile, but their GWP100 value is still quite high for many application. Therefore in the present invention it is preferred to use heat exchange fluids which are essentially free from these compounds.

For "essentially free" it is intended that the heat exchange fluid in the present invention comprises less than 5%, preferably less than 1%, more preferably less than 0.1% of a given component (all percentages are expressed as weight percent of the total of the heat exchange fluid).

The method of the invention can be used to exchange heat with any object. The method of the invention is particularly useful when the object is an electronic computing equipment such as e.g. computer servers. In fact the method of the present invention employs heat transfer fluids which are dielectric and non corrosive so that it can also be used in systems using the so called “immersion cooling” or “direct contact cooling”. In these systems the fluids are placed in direct contact with the electronic circuit boards. Such fluids at their working temperature can be gaseous, liquids (single phase immersion cooling) or be in a gas/liquid equilibrium (i.e. around the boiling point of the liquid, in the so called “two phase immersion cooling”).

In immersion cooling, electronic computer equipment such as CPUs, GPUs, Memory, and other electronics, including complete servers, are completely immersed in a thermally conductive dielectric liquid or coolant, which temperature is controlled through the use of a circulation system which pumps the liquid trough pipes and to heat exchangers or to radiator type coolers to reject the heat from the coolant.

Server immersion cooling is becoming a popular solution for server cooling solution, as it allows to drastically reduce energy usage through the elimination of the expensive air conditioning infrastructure. These systems are replaced with efficient low speed liquid circulation pumps and simpler heat exchanger and/or radiator systems.

The temperatures used in liquid immersion cooling are determined by the highest temperature at which the devices being immersed can reliably operate. For servers this temperature range is typically between 15 to 65° C., however in some cases this range is extended up to 75° C.

Current commercial applications for immersion cooling range from data center oriented solutions for commodity server cooling, server clusters, HPCC applications and Bitcoin Mining and mainstream cloud-based and web hosting architectures. Liquid immersion cooling is also used in the thermal management of computing equipment related to LEDs, Lasers, X-Ray machines, and Magnetic Resonance Imaging devices.

The method of the present invention is preferably suitable for the so called “single phase immersion cooling”. The compounds of the invention exist as liquids in a broad range of temperatures and are therefore suitable for open bath systems where the heat exchange composition remains liquid in all phases of operation. Typically the heat transfer fluid is pumped to an external heat exchanger where it is cooled (or heated in case of need) and recirculated into the bath. A more or less sophisticated control system may be present controlling the instant temperature of the fluid and the temperature of the servers optimizing the fluid temperature in each moment. The low vapour pressure of the compounds with longer Rf chains allows to minimize evaporation and loss of the compounds.

Still in the field of computer equipment cooling, the method of the invention can also be used in non immersion cooling system where the heat exchange fluid is circulated in a closed system and brought in thermal contact with the processors through plates of thermally conductive materials, such as the server cooling solutions produced by Ebullient under the name of “module loops”. The use of a dielectric fluid is anyway beneficial because the risk of leakages is always present and conductive liquids may have destructive effects on the electronics.

The method of the invention can also find application for example in the semiconductor industry where temperature control during manufacturing of semiconductor devices is of great importance. In this case the object which exchanges heat with the heat transfer fluid is a semiconductor device. Temperature control units (TCUs) are used all along the production line for the fabrication of semiconductor devices, and use heat transfer fluids to remove unwanted heat during steps like wafer etching and deposition processes, ion implantation and lithographic processes. The heat transfer fluid is typically circulated through the wafer mounts and each process tool which requires temperature control has its own individual TCU.

Some tools of particular importance which include TCUs are silicon wafer etchers, steppers and ashers. Etching is performed using reactive plasma at temperatures ranging from 70° C. to 150° C. and the temperature of the wafer must be controlled precisely during the plasma treatment. Following the plasma treatment the etched parts are normally immersed in a solvent which removes the etched parts. This second step does not normally require temperature control as it is performed at mild or ambient temperature. When referring to an “etcher” in the present application, it is intended the equipment wherein the plasma treatment at high temperature is performed and which therefore requires a TCU.

Steppers are used in the photolithography of wafers to form the reticules which are then used to expose the photosensitive mask. This process is carried out at temperatures between 40° C. and 80° C., however temperature control is extremely important as the wafer need to be maintained at a precise fixed temperature (+/−0.2° C.) along the process to ensure good results.

Ashing is a process where the photosensitive mask is removed from the wafer and is performed at temperatures from 40° C. to 150° C. The system uses plasma and also here precise temperature control is particularly important.

Another relevant process is plasma enhanced chemical vapour deposition (PECVD) wherein films of silicon oxide, silicon carbide and/or silicon nitride are grown on a wafer within a chamber. Also in this case, while the temperature at which this step is performed can be selected in the range between 50° C. and 150° C., during the deposition process the wafer must be kept uniformly at the selected temperature.

In a semiconductor device production facility typically each Etcher, Asher, Stepper and plasma enhanced chemical vapour deposition (PECVD) chamber has its own TCU wherein a heat transfer fluid is recirculated.

Another process step where heat transfer fluids are used in the manufacturing of semiconductor devices is vapour phase reflow (VPR) soldering. This is the most common method used to connect surface mount devices, multi chip modules and hybrid components to circuit boards. In this method the soldering material is applied in paste form and then the semiconductor device e.g. an unfinished circuit board is placed in a closed chamber with heat transfer fluid at its boiling point in equilibrium with its vapour phase. The fluid in vapour phase transfers heat to the soldering paste which then melts and stabilize the contacts. In this case the fluid is in direct contact with the circuit board so that it must be dielectric and non corrosive. For this application is important that the heat transfer fluid comprises compounds having a boiling point which is sufficient to melt the soldering paste.

Another system which is a key part of the production process of many semiconductor devices is thermal shock testing. In thermal shock testing a semiconductor device is tested at two very different temperature. Different standards exist, but in general the test consists in subjecting the semiconductor device to high and low temperatures and then testing the physical and electronic properties of the device. Typically the semiconductor device to be tested is directly immersed alternatively in a hot bath (which can be at a temperature of from 60° C. to 250° C.) and a cold bath (which can be typically at a temperature of from −10° C. to −100° C. or from −10 to −40° C.). The transfer time between the two bath must be minimized, generally below 10 seconds. Also in this test the fluid making up the baths goes in direct contact with the device and therefore must be dielectric and non corrosive. In addition, to avoid contamination of the baths, it is highly preferable that the same fluid is used both in the cold and in the hot bath. Therefore heat transfer fluids which exist as liquid in a broad range of temperatures are preferred.

Heat transfer fluids for use in the manufacturing of semiconductor devices are typically liquids which are dielectric, non corrosive, and exist in the liquid state in a broad range of temperatures with relatively low viscosity which makes them easily pumpable.

The method of the invention can be used in all the steps of the manufacturing of semiconductor devices which require the semiconductor device to exchange heat with a heat transfer fluid. In particular when using semiconductor processing equipment such as an Etcher, an Asher, a Stepper and a plasma enhanced chemical vapour deposition (PECVD) chamber, each one of these equipment requires precise temperature control and/or heat dissipation and therefore they include temperature control units (TCUs) which can include the selected heat transfer fluid of the method of the invention.

Additionally in thermal shock testing, which is an integral part of semiconductor device manufacturing because only those devices which pass the test are processed further, the semiconductor device is cooled and heated using at least two baths made of heat transfer fluids, a cold one typically at a temperature of from −10 to −100° C., or from −10 to −40° C. and a hot one typically at a temperature of from 60° C. to 250° C. The method of the invention can be advantageously used selecting the appropriate compound or blend of compounds according to the general formula (I) for making up the heat transfer fluid for the baths. Preferably the heat transfer fluid should be selected so that the same heat transfer fluid can be used in both bath thanks to the large temperature range in which the fluid is in liquid state, so that there is no risk of cross contamination of the baths.

The method of the invention can also find application in vapor phase soldering, in fact the selected heat transfer fluid of the method of the invention can be formulated so to have a boiling point in line with that of the soldering paste, so that a semiconductor device comprising soldering paste which still has to be “cured” can be introduced into a closed chamber which contains the selected heat transfer fluid of the method of the invention at its boiling point in equilibrium with its heated vapors. The heated vapors will transfer heat to the semiconductor device thereby melting the soldering paste and therefore fixing the contacts as needed.

An additional advantage is that a single heat transfer fluid can be used in multiple applications potentially allowing the use of a single heat transfer fluid across an entire semiconductor devices manufacturing facility.

Another area wherein the method of the present invention can find application is the thermal management of batteries, in particular rechargeable batteries such as vehicle batteries for cars, trams, trains and the like.

Currently, most of the development in the field of rechargeable batteries, in all industry segments, is focused on Lithium-ion based batteries which are based on different types of lithium salts. Batteries based on Lithium Manganese Oxide, Lithium Iron Phosphate and Lithium Nickel Manganese Cobalt Oxide find application e.g. in vehicles, power tools, e-bikes, and the like. Batteries based on Lithium Cobalt Oxide are typically used in smaller sizes and less intensive applications such as cell phones, portable computers and cameras. Batteries based on Lithium Nickel Cobalt Aluminum Oxide and Lithium Titanate are being considered in applications requiring high power and/or capacity such as electric powertrain and grid storage. Naturally also new technologies, outside the realm of Lithium-ion based batteries, are being explored and continuously developed. The method of the present invention is not linked to a particular battery technology and is applicable to both current and future generations of battery systems.

Differently from conventional power systems, batteries, and in particular rechargeable batteries, have strict requirements for their working environment. Batteries tend to operate in the best conditions within a relatively narrow range of temperatures.

In general low temperatures have an effect on the battery chemistry slowing down the reaction rate and therefore reducing the electricity flow when charging or discharging. High temperatures increase the reaction rate and at the same time also increase energy dissipation thus generating even more excess heat possibly causing an uncontrolled increase of Temperature which can cause irreversible damage to the cell. For a typical Li-ion battery a temperature above 80° C., even only in a part of its structure, can start exothermal chemical reactions which cause a further temperature increase of the battery, ultimately leading to a complete collapse of the battery with risk of fire and explosion.

On the other hand, the practical applications of batteries require them to be efficient in a much broader range of temperatures. For example vehicles batteries need to function properly in any environment where people is expected to use them, so that they need to be operative in a temperature range from −20° C. to +40° C. and beyond. In addition to that, charge and discharge cycles of batteries can generate heat within the battery itself making it even more difficult to maintain the battery within an acceptable temperature range.

Indicative figures for a typical Li-ion battery suggest that the usable range is normally from −20° C. to 60° C., but a good power output is only obtained from 0° C. to 40° C., where optimal performance is only obtainable from 20° to 40° C. Temperature also affects battery duration, in fact the number of charge/discharge cycles a battery can withstand before being considered exhaust go down quickly below 10° C. due to anode plating, and above 60° C. due to the deterioration of the electrode materials. The temperature ranges for optimal performance may be different for different battery chemistries and constructions, however all current commercial batteries share a relatively narrow temperature window where their performance is optimal. It is also important in general to ensure that the entire battery is kept uniformly at the same temperature without hot or cold zones, as this can reduce its lifetime and safety.

For this reason it is nowadays standard to integrate a Battery Thermal management System (BTMS) within commercial battery assemblies, especially when safety, reliability and lifetime of the battery are a significant concern. These BTMSs can be more or less complex, depending on the type of battery, however one common element is the presence of a heat transfer fluid such as a gas or a liquid which exchanges heat with the battery thus heating or cooling it.

Battery thermal management systems (BTMSs) are therefore extremely important, especially in applications requiring high power, and high reliability such as vehicles batteries. A BTMS can be more or less complex, depending on the application, but each BTMS has at least a function to cool the battery when its temperature is too high and a function to heat the battery when its temperature is too low, typically using a heat transfer fluid which exchanges heat with the battery. Other common features in BTMSs are an insulation system, to reduce the effect of the external environment on the battery temperature, and a ventilation system which helps dissipating hazardous gases which may develop within the battery pack. However the method of the present invention relates specifically to the heat exchange function of a BTMS and can be applied easily to any BTMS and integrated with its other functions and features.

BTMSs using a liquid as heat transfer fluid are common because liquids can transfer a larger amount of heat more quickly than gases. Typically the fluid is circulated by a pump within a closed system which is in thermal contact with the battery and with a second system which has the function of heating and/or cooling the fluid to the desired temperature. This second system may comprise any combination of a refrigeration system and a heating system or may combine heating and cooling functions in a heat pump. The circulating fluid absorbs heat from or release heat to the battery and then it is circulated in said second system to bring the fluid back to the desired temperature. A more or less sophisticated control system may be present controlling the instant temperature of the fluid and the temperature of the battery optimizing the fluid temperature in each moment.

In some systems the fluid which is circulated in the system can go in direct contact with the battery cells which are then immersed in it. Clearly in these cases the fluid must be dielectric in order to protect the battery cells and their electronic components. In other cases the heat transfer fluid is circulated in a separate closed system which only exchanges heat by indirect contact trough e.g. a heat exchange plate made of metal or other thermally conductive material. A dielectric fluid may be beneficial also in this type of systems because closed systems have anyway a high risk of leakages.

Particularly for high power batteries thermal management systems based on fluids, liquids in particular, are being used and the method of the invention offers an improved thermal management at a lowered $GWP_{100}$.

Beyond the cited applications, the method of the invention can be also adapted to any heat exchange method e.g. for heating or cooling compartments (e.g. food stuffs compartments) including those on board of aircrafts, vehicles or boats, for heating or cooling industrial production equipment, for heating or cooling batteries during their operations, for forming thermostatic baths.

As mentioned in the introduction, heat transfer fluids used in these fields include fluorocompounds. In particular hydrofluorotethers have found application in these fields due to their chemical inertness, dielectricity, wide range of T in which they are liquid and pumpable (typically having a viscosity between 1 and 50 cps at the temperatures of use), low flammability and relatively low GWP.

Commercially available hydrofluoroethers for use in these fields are e.g. those from the Novec™ series of 3M which combine all these properties with a relatively low $GWP_{100}$ of from about 70 to 300.

Still, GWP is a critical property nowadays also due to the regulatory environment so that there is always a demand to develop new heat exchange fluids which have even lower GWP than then currently commercialized hydrofluoroethers.

The applicant has surprisingly found that the heat transfer fluid employed in the method of the invention is non-flammable, provides efficient heat transfer, can be used across a wide temperature range and has equal or improved dielectric properties with respect to other hydrofluoroethers commercialized as heat transfer fluids. Surprisingly heat transfer fluids used in the invention have an extremely low $GWP_{100}$, in general lower than 50 and for some materials even lower than 30, as it will be shown below in the experimental section. This is a particularly unexpected result and in fact previous reviews such as Hodnebrog et. al. cited above did not investigate or propose pentaeritrytol derivatives as low GWP compounds.

Therefore, using these selected chemical compounds in accordance to the general formula (I), heat transfer fluids can be formulated which have a GWP100 value of less than 50, preferably less than 30, The heat transfer fluids according to the invention also have low toxicity, showing good heat transfer properties and relatively low viscosity across the whole range. Also, the fluids of the invention have good electrical compatibility, i.e. they are non corrosive, have high dielectric strength, high volume resistivity and low solvency for polar material. The electrical properties of the fluids of the invention are such that they can be used in immersion cooling system for electronics in direct contact with the circuits as well as in indirect contact applications using loops and/or conductive plates.

The heat transfer fluids for use in the method of invention preferably comprise more than 5% by weight of one or more compounds according to formula (I) above, more preferably more than 50% by weight, even more preferably more than 90% by weight. In one embodiment the heat transfer fluid is entirely made of one or more compounds according to the general formula above.

In some embodiments the heat transfer fluid of the invention comprises a blend of chemical compounds according to formula (I).

The method of the invention can be applied to any heating and/or cooling system which uses a heat transfer fluid and in particular to all those exemplified in the description. Particularly for the temperature control of electronic computing equipment, both in immersion cooling of such equipment, where the electronic circuit boards are directly immersed in the liquid, to distributed systems where the fluids are distributed to cooling elements capable of exchanging heat with boards such as plates of thermally conductive materials such as metals and metallic alloys.

Other applications are in the thermal management of batteries, particularly rechargeable batteries, e.g. for vehicles such as cars, trams, trains.

Further applications are found in the semiconductor industry where the object of the heat exchange is a semiconductor device, such as in temperature control units (TCUs) for etchers, ashers, steppers and PECVD chambers, in thermostatic baths for thermal shock testing and in vapor phase soldering.

In another aspect the present invention also encompasses an apparatus comprising an electronic computing equipment and a heat transfer fluid wherein said heat transfer fluid comprises one or more chemical compounds having the general formula (I).

In a further aspect the present invention relates to an apparatus comprising a battery, preferably a rechargeable battery, a thermal management system for said battery, said thermal management system for said battery comprising a heat transfer fluid exchanging heat with said battery, wherein said heat transfer fluid comprises one or more chemical compounds having the general formula (I).

Should the disclosure of any patents, patent applications, and publications which are incorporated herein by reference conflict with the description of the present application to the extent that it may render a term unclear, the present description shall take precedence.

The invention will be now described in more detail with reference to the following examples whose purpose is merely illustrative and not limitative of the scope of the invention.

Standards:

Measurement of electrical properties were performed according to the following standards:

Volume resistivity—ASTM D5682-08[2012]

Dielectric strength—ASTM D877/D877M-13

Dielectric constant—ASTM D924-15

EXAMPLES

Example 1—Synthesis of C(CH2-O-CF2-CHF2)4 (HFE4)

1.12 l of anhydrous Acetonitrile and 182 g 2,2-bis(hydroxymethyl)propane-1,3-diol (PENTA reagent grade) were introduced in a 2 l stirred stainless steel pressurized reactor. 75 g KOH potassium hydroxide were then added, the reactor was closed and flushed four times with nitrogen. Then a total of 600 g of TFE (tetrafluoroethylene) were fed to the reactor at 7 bar and an average rate of 36 g/min while regulating the internal temperature around 65° C. by means of a temperature control. After 3.3 hours the reactor was then purged of TFE and, while cooling to 25° C., flushed four times with nitrogen.

1580 g of a liquid mixture was discharged from the reactor. This liquid mixture was added 8 l of demineralized water and scrubbed in a stirred 10 l glass vessel for about 4 h at 25° C. The mixture was then left to settle overnight.

745 g of organic liquid were then separated as the bottom layer. This liquid was freed from residual acetonitrile distilling in a 1 lt round-bottom flask equipped with a 40 cm Vigreux column and a Claisen condenser. Pure hydrofluoroether was collected at 90° C. head temperature under a vacuum of 0.5 mbar. The product has been identified with its 19F-NMR spectrum (−138.6 ppm doublet of triplet J=53 Hz J=5 Hz Int.=1; −93.7 ppm quartet J=5 Hz Int.=1) and 1H-NMR spectrum (4.21 ppm singlet Int.=2; 6.24 ppm triplet of triplet J=53 Hz, J=3 Hz Int.=1) and its GC-MSD mass spectrum. GC-TCD separation on a CP-SIL8CB 0.45 mic capillary column elutes a single peak 99.5% signal area.

640 g of hydrofluoroether pure $C(CH_2—O—CF_2—CHF_2)_4$ (HFE4) were obtained.

GWP Measurement

The $GWP_{100}$ for $C(CH_2—O—CF_2—CHF_2)_4$ (HFE4) has been determined at the University of Oslo according to established procedures, by measuring the integrated absorption cross section of infrared spectra over the region 3500-500 cm-1, the kinetic of reaction with OH radicals, and calculating the consequent atmospheric lifetime and radiative forcing efficiency. As a result of these measurements a $GWP_{100}$ of 28 has been obtained. The infrared absorption cross section was predicted in B3LYP/6-31G quantum chemistry calculations. The HFE4 reaction with OH radicals was determined at atmospheric pressure and 298 K to be $$k_{HFE4+OH}=0.95\cdot10^{-14}\ \mathrm{cm^3\ molecule^{-1}\ s^{-1}}$$

employing Novec 7200 as reference.

Electric and thermal properties of in comparison with other commercially available hydrofluoroethers:

| | $GWP_{100}$ | Volume resistivity (ohm cm−1) | Dielectric strength (kV) | Dielectric constant |
|---|---|---|---|---|
| NOVEC 7200 | 70 | 1.00E+08 | 30 | 7.3 |
| NOVEC 7000 | 530 | 1.00E+08 | 40 | 7.4 |
| HFE 4 | 28 | 2.00E+11 | 24.2 | 6.72 |

Other physical properties of compounds according to the invention:

| | HFE 4 |
|---|---|
| Dielectric constant @1 kHz | 6.72 |
| Dielectric strength kV | 24.2 |
| Volume resistivity Ohm * cm | 2.00E+11 |
| Kin viscosity (25° C.) cSt, | 35 |
| density (25° C.) g/cm3, | 1.58 |
| heat of vaporization kcal/kg | 35 |
| surface tension mN/m | 29 |
| pour point ° C. | −45 |
| Boiling point ° C. | 270 |

The results show how the compounds of the invention have overall equal or improved properties when compared with existing commercial materials used for similar purposes and have lower GWP. Heat transfer fluids comprising these compounds can be used in all the mentioned applications involving heat exchange with an electronic computing equipment, batteries or semiconductor devices.

The invention claimed is:

1. A method for exchanging heat with an object, the method comprising contacting a heat transfer fluid with the object, wherein the object is an electronic computing equipment and said heat transfer fluid comprises one or more hydrofluoroether chemical compounds having the general formula:

(I)

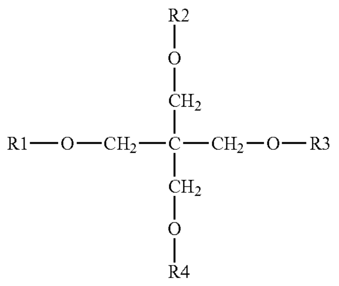

wherein:

$R_1$, $R_2$, $R_3$, $R_4$ can be the same or different, linear or branched, partially fluorinated alkyl groups having a $C_1$-$C_6$ carbon chain and wherein the heat transfer fluid has a $GWP_{100}$ of less than 60 and is essentially free of CFCs, HFCs and HCFCs.

2. The method according to claim 1 wherein the one or more hydrofluoroether chemical compounds of general formula (I) make up at least 5% by weight of the heat transfer fluid.

3. The method according to claim 1 wherein the electronic computing equipment is one or more servers.

4. The method according to claim 1 wherein the electronic computing equipment comprises one or more electronic circuit boards, the method comprising the step of contacting directly the electronic circuit boards with the heat transfer fluid.

5. The method according to claim 1 which is a method of single phase immersion cooling.

6. A method for exchanging heat with an object, wherein the object is a battery, the method comprising contacting a heat transfer fluid with the object, said heat transfer fluid comprises one or more hydrofluoroether chemical compounds having the general formula:

(I)

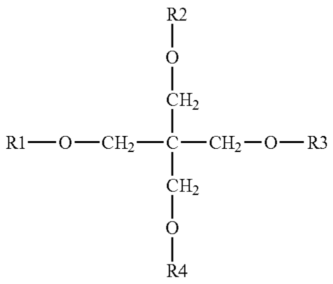

wherein:

$R_1$, $R_2$, $R_3$, $R_4$ can be the same or different, linear or branched, partially fluorinated alkyl groups having a $C_1$-$C_6$ carbon chain and wherein the heat transfer fluid has a $GWP_{100}$ of less than 60 and is essentially free of CFCs, HFCs and HCFCs.

7. The method according to claim 6 wherein the rechargeable battery is a rechargeable vehicle battery.

8. A method for exchanging heat with an object, wherein the object is a semiconductor device, the method comprising contacting a heat transfer fluid with the object, said heat transfer fluid comprises one or more hydrofluoroether chemical compounds having the general formula:

(I)

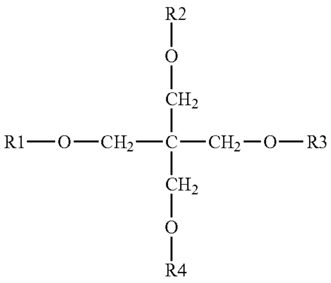

wherein:

$R_1$, $R_2$, $R_3$, $R_4$ can be the same or different, linear or branched, partially fluorinated alkyl groups having a $C_1$-$C_6$ carbon chain and wherein the heat transfer fluid has a $GWP_{100}$ of less than 60 and is essentially free of CFCs, HFCs and HCFCs.

9. The method of claim 8, wherein the contacting is performed during manufacturing of the semiconductor device.

10. The method of claim 1, wherein the contacting comprises the heat transfer fluid transferring heat directly with the object.

* * * * *